Figure 1:
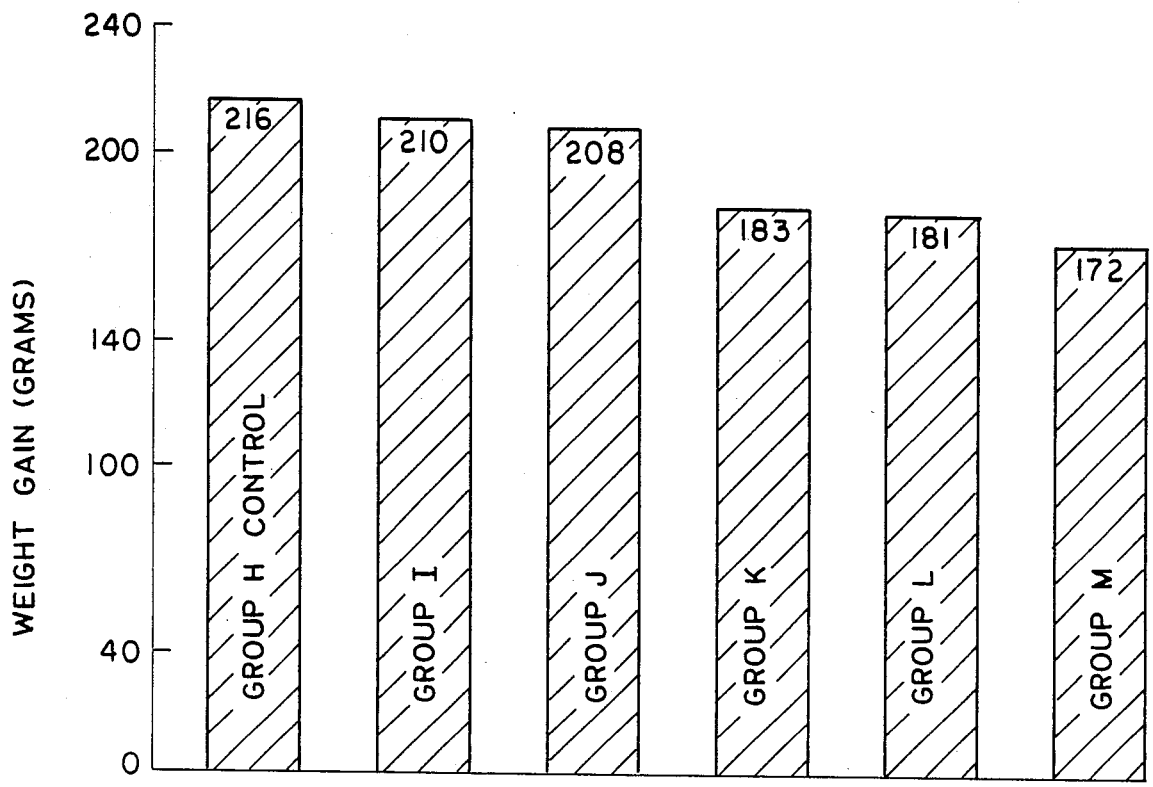

United States Patent [19]

Stanko

[11] Patent Number: 4,548,937

[45] Date of Patent: * Oct. 22, 1985

[54] METHOD FOR PREVENTING BODY FAT DEPOSITION IN MAMMALS

[75] Inventor: Ronald T. Stanko, Pittsburgh, Pa.

[73] Assignee: Montefiore Hospital, Pittsburgh, Pa.

[*] Notice: The portion of the term of this patent subsequent to Sep. 28, 1999 has been disclaimed.

[21] Appl. No.: 529,403

[22] Filed: Sep. 6, 1983

Related U.S. Application Data

[63] Continuation-in-part of Ser. No. 346,181, Feb. 9, 1982, Pat. No. 4,415,576, which is a continuation-in-part of Ser. No. 249,812, Apr. 1, 1981, Pat. No. 4,351,835.

[51] Int. Cl.⁴ ............................................. A61K 31/19
[52] U.S. Cl. ..................... 514/251; 514/557; 514/909
[58] Field of Search ............................... 424/252, 317

[56] References Cited

U.S. PATENT DOCUMENTS 4,351,835  9/1982  Stanko ................................. 424/252
4,415,576  11/1983 Stanko ................................. 424/252

OTHER PUBLICATIONS

Chemical Abstracts 67: 19055b, (1967); (Gershbein).
Gershbein, Acta Hepto-Spenol, 13(6) 363–369, (1960).

*Primary Examiner*—Leonard Schenkman
*Attorney, Agent, or Firm*—Thomas H. Murray; Clifford A. Poff

[57] ABSTRACT

A method for reducing the weight gain in mammals by orally administering over a prolonged period therapeutically effective amounts of pyruvate to which may be added riboflavin. The method also has the effect of increasing the body protein concentration.

7 Claims, 2 Drawing Figures

METHOD FOR PREVENTING BODY FAT DEPOSITION IN MAMMALS

CROSS-REFERENCE TO RELATED APPLICATIONS

This application is a continuation-in-part of application Ser. No. 346,181, filed February 9, 1982 now U.S. Pat. No. 4,415,576 which is a continuation-in-part of application Ser. No. 249,812, filed Apr. 1, 1981, now U.S. Pat. No. 4,351,835, issued Sept. 28, 1982.

BACKGROUND OF THE INVENTION

In U.S. Pat. No. 4,158,057, issued June 12, 1979, a method is described for preventing the accumulation of excessive fatty deposits in the livers of mammals. It has long been known that ingestion of ethyl alcohol in mammals, including man, frequently results in the accumulation of excessive fatty deposits in the liver. In many cases, this accumulation tends to become irreversible and may lead to serious consequences, particularly alcohol-induced hepatitis and, ultimately, cirrhosis.

The invention described in the aforesaid U.S. Pat. No. 4,158,057 resides in the discovery that excessive fatty deposits in the liver can be reduced or prevented from occurring by administering a therapeutic composition consisting of a mixture of pyruvate and dihydroxyacetone to which may be added riboflavin. These substances are natural metabolites which occur in the body as a result of normal digestive processes. Heretofore, however, there has been no appreciation of any correlation between the accumulation of fatty deposits in the liver, usually due to the ingestion of alcohol, and the accumulation of fat in other parts of the body.

SUMMARY OF THE INVENTION

It has been found, quite surprisingly, that pyruvate disclosed in U.S. Pat. No. 4,158,057, when administered for a relatively long period of time, at least 15 days or more, results in a reduction of the rate of hepatic triglyceride generation and body fat deposition for a given diet. Pyruvate is thus useful for impeding overweight conditions in mammals, with or without ingestion of ethanol.

Additionally, it has been found that prolonged ingestion of pyruvate, with or without riboflavin, increases the glycogen-storage capabilities of the liver. Stored glycogen is thus increased for subsequent release into the bloodstream. Stored glycogen has been reported to increase the performance and endurance of athletes.

A further surprising discovery of the present invention is that there is a decrease in the total body fat with a secondary inhibition of weight gain in mammals. Prolonged ingestion of pyruvate alone or a mixture of pyruvate and dihydroxyacetone, with or without riboflavin, actually changes the body composition to the extent that body fat is actually decreased by the inhibitory effect of the lipotropic agent on fat metabolism. Moreover, a significant finding of the present invention is a small but clinically substantial increase in body protein concentration induced by the lipotropic agent.

Figure 2:
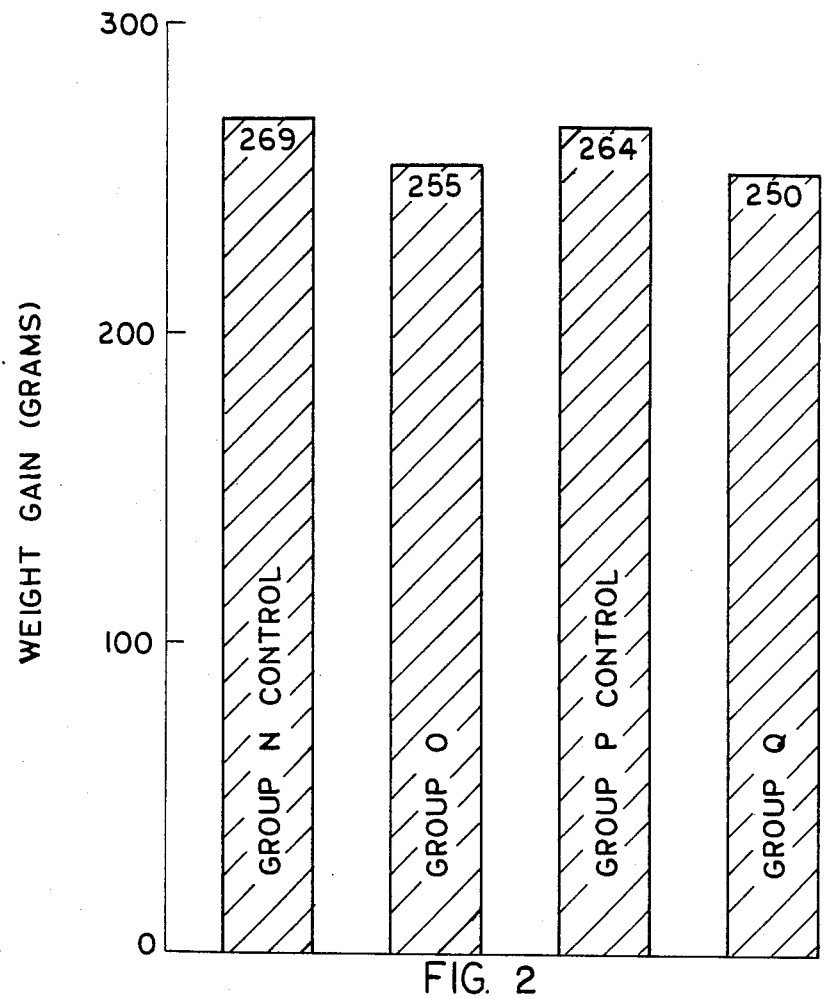

The above and other objects and features of the invention will become apparent from the following detailed description taken in connection with the accompanying drawings which form a part of this specification, and in which:

FIG. 1 is a bar graph illustrating the effect of the present invention on weight gain; and FIG. 2 is another bar graph illustrating the effect of the present invention on weight gain.

Heretofore, as described in my early U.S. Pat. No. 4,158,057, pyruvate and dihydroxyacetone were found equally ineffective when used alone, but when used in combination, the mixture of these two agents produces a marked reduction in the fatty acid concentration in mammalian livers. The addition of riboflavin to the mixture further enhances the effect. Pyruvate (pyruvic acid-$CH_3COCOOH$) is a product of the metabolism of glucose and some amino acids, while dihydroxyacetone (($CH_2OH)_2CO$) is a product of the metabolism of fatty acids and certain amino acids. These substances are, therefore, both natural metabolites which are normally present in the body, while riboflavin (Vitamin B2) is also present in the body. All of these substances, therefore, are natural products which are normally harmless.

To demonstrate the efficacy of the present invention, a group of experiments extended over a period of 28 days, the results of which are shown in FIG. 1. Rats were divided into six groups ranging from 6 to 9 in number. A standard laboratory diet containing 15% protein, 28% fat and 57% carbohydrate was fed to the rats. The first group (Group H) was fed the standard laboratory diet to which 248 grams of dextrin per 1000 grams of diet was added. Group H was designated a control group. The second group (Group I) received the same diet as Group H but with the addition of 12.4 grams of riboflavin per 1000 grams of diet. The third group (Group J) received the standard laboratory diet to which was added 124 grams of dextrin per 1000 cubic centimeters of the diet and 124 grams of dihydroxyacetone per 1000 grams of diet. The fourth group (Group K) received the standard laboratory diet to which was added 124 grams of pyruvate per 1000 grams of diet and 124 grams of dextrin per 1000 grams of diet. The fifth group (Group L) received the standard laboratory diet to which was added 124 grams of pyruvate per 1000 grams of diet and 124 grams of dihydroxyacetone per 1000 grams of diet. The sixth group (Group M) received the same diet as Group L but with the addition of 12.4 grams of riboflavin per 1000 grams of diet.

As shown in FIG. 1, Group H, control, experienced a weight gain of 216 grams in 28 days which, when compared with the weight gain of 210 grams by the animals in Group I, shows an insignificant difference in the weight gain. The same is true with respect to the animals comprising Group J which experienced a weight gain of 208 grams. However, with respect to the animals comprising Group K, the surprising result was that the weight gain of 183 grams as compared with control at 216 grams shows a significant inhibition against weight gain. Surprising and similar results were discovered by comparing the weight gain of 181 grams by Group L which demonstrates that pyruvate alone is therapeutically effective for weight inhibition substantially to the same extent that the therapeutic mixture of pyruvate and dihydroxyacetone is effective as shown by comparing the weight gains by Groups H and L. The inhibition against weight gain shown by comparing the results of Group M at 172 grams versus control, Group H, at 216 grams shows that the addition of riboflavin in a mixture of pyruvate and dihydroxyacetone in the diet increases the effect against an expected weight gain. The addition of only riboflavin to the diet as shown by comparing Group I with control, Group H, reveals a 6-gram difference; whereas the addition of riboflavin to the mixture of pyruvate and dihydroxyacetone in the diet as shown by the results of Group M as compared with Group L shows a 9-gram loss for an expected weight gain.

Similar results are demonstrated by the bar graph of FIG. 2 in which Group N and Group P were the control group. Group O received the same diet as control, Group N, but with the addition of 124 grams of pyruvate per 1000 grams of diet and 124 grams of dextrin per 1000 grams of diet. Group Q received the same diet as control, Group P, but with the addition of 124 grams of pyruvate per 1000 grams of diet and 124 grams of dihydroxyacetone per 1000 grams of diet. The experiment extended over a period of 28 days. Groups N and O each comprised 9 rats and Groups P and Q each comprised 6 rats. The animals were fed the same standard laboratory diet except as just described. The inhibition against a weight gain was smaller as seen by a comparison of the bar graphs for Group N with Group O and Group P with Group Q. However, with each of the Groups N and O there was a standard error of 11 and with each of the Groups P and Q there was a standard error of 6. Notwithstanding the large standard error, the results again demonstrate the effectiveness of pyruvate alone as a lipotropic agent.

Although the invention has been shown in connection with certain specific embodiments, it will be readily apparent to those skilled in the art that various changes can be made to suit requirements without departing from the spirit and scope of the invention.

I claim as my invention:

1. A method for controlling the weight in a mammal, which comprises administering orally to an intact mammal in need thereof a therapeutically effective amount of pyruvate to induce a weight loss or to reduce an expected weight gain from a given diet.

2. The method of claim 1 in which riboflavin is administered as a mixture with pyruvate.

3. The method of claim 1 wherein pyruvate is administered for at least 15 days.

4. The method according to claim 1 wherein pyruvate is administered for 60 days.

5. The method according to claim 1 wherein body fat deposition in said mammal is effectively reduced by administering pyruvate.

6. A method for increasing the protein concentration in the body of a mammal, which comprises administering orally to an intact mammal in need thereof a therapeutically effective amount of pyruvate for a period of at least about 15 days to increase body protein concentration.

7. The method according to claim 6 in which riboflavin is administered as a mixture with pyruvate.

* * * * *